US008748837B2

(12) United States Patent
Carasco et al.

(10) Patent No.: US 8,748,837 B2
(45) Date of Patent: Jun. 10, 2014

(54) NON-INTRUSIVE METHOD FOR DETECTION OF CHEMICAL ELEMENTS

(75) Inventors: Cedric Carasco, Vinon-sur-Verdon (FR); Bertrand Perot, Venelles (FR)

(73) Assignee: Commissariat a l'Energie Atomique et aux Energies Alternatives, Paris (FR)

(*) Notice: Subject to any disclaimer, the term of this patent is extended or adjusted under 35 U.S.C. 154(b) by 214 days.

(21) Appl. No.: 13/133,938

(22) PCT Filed: Dec. 14, 2009

(86) PCT No.: PCT/EP2009/067102
§ 371 (c)(1),
(2), (4) Date: Jun. 9, 2011

(87) PCT Pub. No.: WO2010/069931
PCT Pub. Date: Jun. 24, 2010

(65) Prior Publication Data
US 2011/0243306 A1      Oct. 6, 2011

(30) Foreign Application Priority Data
Dec. 15, 2008 (FR) ...................... 08 58564

(51) Int. Cl.
*G01N 23/202* (2006.01)
*G01N 23/222* (2006.01)
(52) U.S. Cl.
CPC ............ *G01N 23/222* (2013.01); *G01N 23/202* (2013.01)
USPC ................. 250/389; 250/390.01; 250/390.04; 250/390.07

(58) Field of Classification Search
CPC ........................... G01N 23/222; G01N 23/202
USPC ........ 250/269.4, 389, 390.01, 390.04, 390.07
See application file for complete search history.

(56) References Cited

U.S. PATENT DOCUMENTS

| | | | |
|---|---|---|---|
| 5,440,118 A * | 8/1995 | Roscoe ...................... 250/269.6 |
| 6,393,085 B1 | 5/2002 | Heller et al. |
| 7,141,804 B1 * | 11/2006 | Akselrod et al. ........... 250/483.1 |
| 2002/0150194 A1 * | 10/2002 | Wielopolski et al. ......... 376/160 |
| 2002/0175288 A1 | 11/2002 | Taleyarkhan |
| 2007/0241283 A1 | 10/2007 | Chu et al. |

OTHER PUBLICATIONS

Sudac, D. et al., "Chemical Composition Identification Using Fast Neutrons," Applied Radiation and Isotopes, vol. 61, Elsevier, Oxford, GB, Jul. 1, 2004, pp. 73-79.

(Continued)

*Primary Examiner* — David Porta
*Assistant Examiner* — Abra Fein
(74) *Attorney, Agent, or Firm* — Nixon Peabody LLP (57) ABSTRACT

A method for detecting the presence of a chemical element in an object by emission of neutrons onto the object, characterized in that the emission of neutrons onto the object is constituted, firstly, by a continuous emission of neutrons originating from an associated particle neutron generator (G1) and, secondly, by an emission of neutron pulses which are superimposed on the continuous emission of neutrons, where the neutron pulses originate from a pulsed neutron generator (G2) which generates neutron pulses of pulse duration T2, where two successive neutron pulses are separated by a duration T4, and where the continuous and pulsed emissions of neutrons on to the object produce a gamma capture radiation and an inelastic gamma radiation.

8 Claims, 5 Drawing Sheets

(56) References Cited

OTHER PUBLICATIONS

Vourvopoulos, G. et al., "A Pulsed Fast-Thermal Neutron System for the Detection of Hidden Explosives," Nuclear Instruments & Methods in Physics Research, vol. B79, Nos. 1/4, Beam Interactions With Materials and Atoms, Elsevier, Amsterdam, NL, Jun. 2, 1993, pp. 585-588.

French Search Report in French Application No. FR 0858564, dated Aug. 5, 2009.

International Search Report and Written Opinion in International Application No. PCT/EP2009/067102, mailed Feb. 8, 2010.

* cited by examiner

NON-INTRUSIVE METHOD FOR DETECTION OF CHEMICAL ELEMENTS

CROSS REFERENCE TO RELATED APPLICATIONS OR PRIORITY CLAIM

This application is a National Phase of PCT/EP2009/067102, filed Dec. 14, 2009, entitled, "METHOD FOR THE NON-INTRUSIVE DETECTION OF A CHEMICAL ELEMENT", and which claims priority of, French Patent Application No. 08 58564, filed Dec. 15, 2008, the contents of which are incorporated herein by reference in their entirety.

TECHNICAL FIELD AND PRIOR ART

The invention concerns a non-intrusive method for detection of at least one chemical element present in a liquid or a solid.

The invention applies, for example, to the detection of an explosive (or explosives), a chemical weapon (or weapons) or a drug (or drugs) in the field of civil security (luggage inspection, freight containers, etc.), to the search for contraband products (customs inspections), to mine clearance (civil security and military applications), and again to the characterisation of materials constituting radioactive waste produced by the nuclear industry.

Various methods are known for the non-intrusive detection of chemical elements. Some of these methods are based on the use of neutron measurements.

Among the methods based on the use of neutron measurements, some identify the chemical elements by detecting capture gamma radiation (n, γ) induced by thermal neutrons, or by detecting inelastic scattering gamma radiation (n, n'γ), or again by detecting gamma radiation following other reactions caused by fast neutrons, namely (n,p), (n,d), (n,t), (n,α), etc. In the remainder of the description, the expression "inelastic gamma radiation" is used for all gamma radiation induced by fast neutrons.

The detection of capture radiation induced by thermal neutrons is more sensitive using a pulsed neutron generator for the emission of the neutrons since the signal-to-noise ratio (where the signal is the capture radiation and the noise is the inelastic radiation) is at its maximum between the pulses. An illustration of this type of detection is given in U.S. Pat. No. 6,393,085 B1. In this document the possible detection of inelastic gamma radiation is also described, this time during the pulses, but such a method has a detection sensibility which is substantially less than by using an associated particle tube (TPA), which enables the inspected object to be located spatially from a neutron flight time measurement, the principle of which is described in detail in patent application US 2007/0241283 A1. In short, each neutron is emitted simultaneously with an α particle and in the opposite direction. The detection of the α particle enables the emission direction of the neutron to be determined, and the measurement of the time separating the detection of the α particle and of the inelastic γ radiation induced by the neutron enables the neutron flight time to be determined. A means is therefore available of locating in 3D the place of interaction, and therefore of eliminating the events produced outside the zone of interest, leading to a substantial improvement of the signal-to-noise ratio compared to pulsed interrogation. However, since the emission of the TPA is continuous it follows that, with this method, detection of the capture radiation is not optimal in signal-to-noise ratio terms. One problem lies in the fact that neither of the two methods, one based on the pulsed tube, the other on TPA, enables the capture radiation and the inelastic radiation to be detected simultaneously with the best possible sensitivity, and consequently all the elements sought to be identified satisfactorily. Once the first method has been accomplished, it is then necessary to accomplish the second method in order to broaden the field of detectable elements, or to improve the level of confidence in relation to the presence of those detectable by both methods. The total duration of a detection operation is consequently relatively long, representing a major disadvantage in terms of safety.

The invention does not have this disadvantage.

Account of the Invention

Indeed, the invention concerns a method for detecting the presence of a chemical element in an object by emission of neutrons on to the object, characterised in that the emission of neutrons on to the object is constituted, firstly, by a continuous emission of neutrons originating from an associated particle neutron generator and, secondly, by an emission of neutron pulses which are superimposed on the continuous emission of neutrons, where the neutron pulses originate from a pulsed neutron generator which generates neutron pulses of pulse duration T2, where two successive neutron pulses are separated by a duration T4, and where the continuous and pulsed emissions of neutrons on to the object produce a gamma capture radiation and an inelastic gamma radiation.

According to an additional feature of the invention, the method includes:

detection, using the associated particle technique, during the T4 durations separating the pulses of duration T2, of the inelastic gamma radiation and of the capture gamma radiation, formation, in a neutron flight time span relative to the object, of a first gamma spectrum on the basis of the inelastic gamma radiation and of the capture gamma radiation detected in the detection step using the associated particle technique, formation, in a time span separated from the neutron flight time span relative to the object or any other neutron flight time span relative to any other object likely to be in the vicinity of the object, of a random background noise spectrum relative to the fortuitous coincidences, on the basis of the inelastic gamma radiation and of the capture gamma radiation detected in the detection step using the associated particle technique, formation, on the basis of the random background noise spectrum relative to the fortuitous coincidences, of a standardised random background noise spectrum over the time span relative to the object, subtraction of the first gamma spectrum and of the standardised random background noise spectrum to form a second gamma spectrum, and a step of searching for the presence of a chemical element in the object on the basis of the second gamma spectrum and of spectra of chemical elements of reference which may be detected in order to deliver a first data item able to reveal the presence or absence of the chemical element in the object.

According to another additional feature of the invention, the method also includes:

detection, using the pulsed neutron interrogation technique, of the capture gamma radiation and of the inelastic gamma radiation, firstly during the T2 pulse durations, and secondly during the T4 durations separating the pulses of duration T2.

formation of a third gamma spectrum, on the basis of the detected gamma capture radiation and inelastic gamma radiation, during the T4 durations, using the pulsed neutron interrogation technique, formation, on the basis of the third gamma spectrum, of a first data item representative of at least one capture line of the chemical element, formation of a fourth gamma spectrum consisting of multiple energy channels, on the basis of the inelastic radiation detected during the T2 pulse durations, using the pulsed neutron interrogation technique, formation of a standardised gamma spectrum on the basis of the fourth gamma spectrum, where the standardised gamma spectrum is formed by multiplying the content of each energy channel of the fourth gamma spectrum by a standardisation factor F roughly proportional to the number of neutrons emitted during a T4 duration, and roughly inversely proportional to the number of neutrons emitted during a T2 duration, formation, on the basis of the standardised gamma spectrum, of a second data item representing an inelastic gamma radiation background noise, a step of subtraction of the first data item and of the second data item, a step of validation of the presence or absence of the chemical element in the object according to the results of the subtraction step, and if the presence of the chemical element is validated in the object, an additional step which delivers a second data item able to confirm or refute the validation of the presence of the chemical element on the basis of the result of the validation step and of weight data relative to the various capture radiation gamma lines of the chemical element, where these weights are attributed according to a probability of detection and a risk of interference associated with each line.

According to yet another additional feature of the invention, the standardisation factor F is given by the following equation:

$$F=(I_4 \times T4)/(I_2 \times T2) \times [(1-TM(T4))/(1-TM(T2))],$$

where TM(T4) and TM(T2) are, respectively, an idle time of an electronic processing unit which process the electrical signals resulting from the detection of the gamma radiation during the T4 durations, and an idle time of an electronic processing unit which process the electrical signals resulting from the detection of the gamma radiation detected during the T2 durations.

According to yet another additional feature of the method of the invention, a decision-making step delivers an alert signal if the first data item or the second data item confirms the presence of the chemical element.

According to yet another additional feature of the invention, if the presence of several chemical elements is confirmed it includes an additional step of calculation of relative proportions of all or part of the chemical elements the presence of which is confirmed.

According to yet another additional feature of the method of the invention, the detection, using the associated particle technique, of the capture gamma radiation and of the inelastic gamma radiation during the T4 durations separating the pulses of duration T2 is undertaken by a detector which is preferentially adapted for the detection of inelastic gamma radiation.

According to yet another additional feature of the method of the invention, the detection, using the pulsed neutron interrogation technique, of the capture gamma radiation and of the inelastic gamma radiation, firstly, during the T2 pulse durations and, secondly, during the T4 durations separating the pulses of duration T2, is undertaken by a detector which is preferentially adapted for the detection of capture gamma radiation.

A simultaneous use of an associated particle neutron generator G1 which emits neutrons continuously and of a pulsed neutron generator G2 which emits neutron pulses apparently has a disadvantage for the detection of capture radiation due to the presence of a residual neutron emission between the pulses of generator G2, this residual emission being due to the continuous emission of generator G1. This residual emission indeed degrades the signal-to-noise ratio (where the signal is the capture radiation and the noise is the inelastic radiation). Advantageously, the method of the invention proposes means to eliminate this disadvantage. In the context of the invention the combined use of generators G1 and G2 then allows, in a single acquisition, measurements which are usable in terms of sensitivity to be obtained, for the capture gamma radiation detected by pulsed neutron interrogation and for the inelastic gamma radiation detected by the associated particle method. The field of the detectable elements is broadened thereby without increasing the acquisition time. In addition, for the elements detectable by both methods, the level of confidence of detection is improved.

With the detection system of the invention it is advantageously possible to use a large proportion of period T of the neutron pulses (typically 95%) to detect simultaneously both types of radiation induced by the thermal neutrons (capture) and by the fast neutrons (inelastic scattering and reactions $(n,\alpha)$, $(n,p)$, etc.)

BRIEF DESCRIPTION OF THE FIGURES

Other features and advantages of the invention will appear on reading a preferential embodiment made in reference to the attached figures, among which.

In all the figures the same references designate the same elements.

DETAILED DESCRIPTION OF PREFERENTIAL EMBODIMENTS OF THE INVENTION

Figure 1:
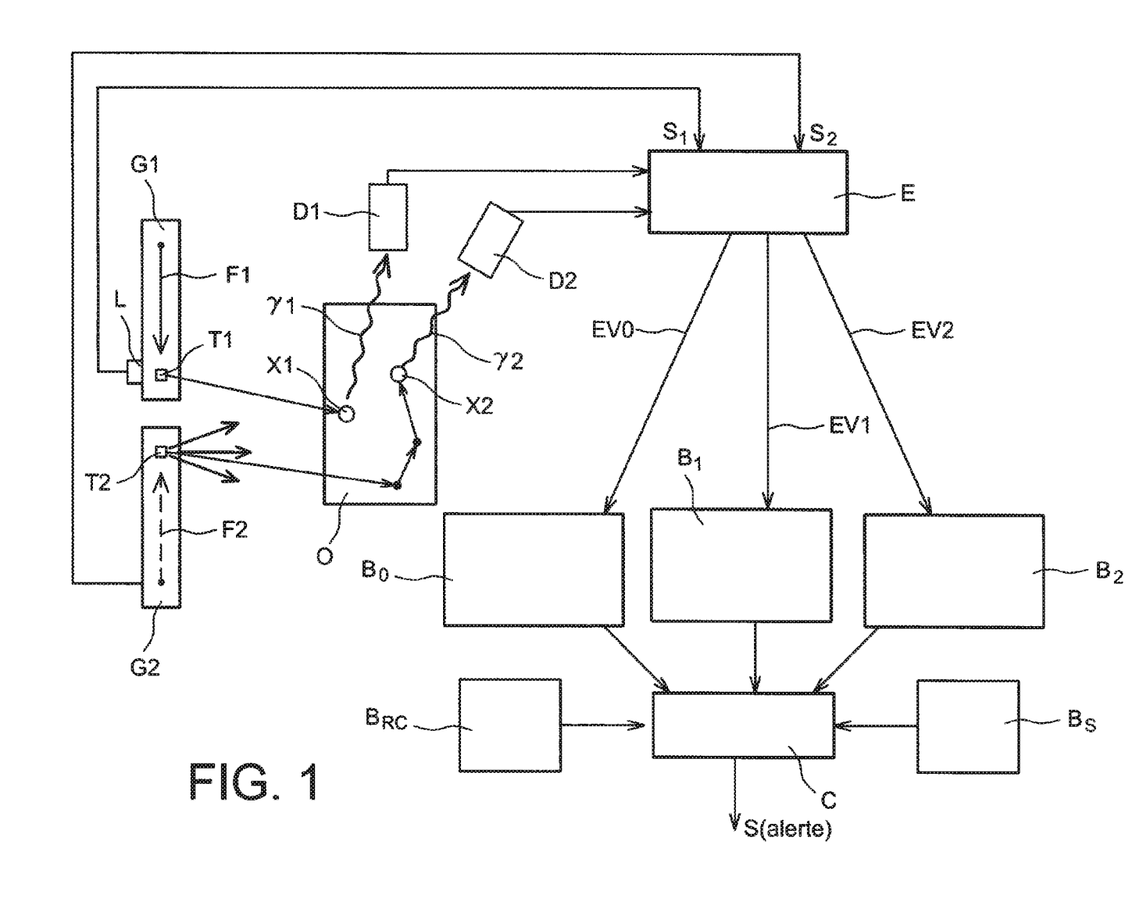
FIG. 1 represents a schematic diagram of a non-intrusive detection system which uses the method of the invention.

FIG. 1 represents a schematic diagram of a non-intrusive detection system which uses the method of the invention.

Around object O which may contain chemical elements to be detected, the detection system of the invention includes an associated particle neutron generator G1, a pulsed neutron generator G2, two detectors D1 and D2, an electronic processing circuit E which processes and shapes the signals originating from the detectors D1 and D2, databases $B_o$, $B_1$, $B_2$ which store the data delivered by the electronic processing circuit E, reference databases $B_{RC}$ and Bs which store, respectively, data relative to the reference capture lines and to inelastic gamma radiation reference spectra, and a computer C which calculates a signal which reveals the presence or absence of chemical element(s) or dangerous products on the basis of the data contained in the databases $B_0$, $B_1$, $B_2$, $B_{RC}$ and $B_S$.

Figure 2:
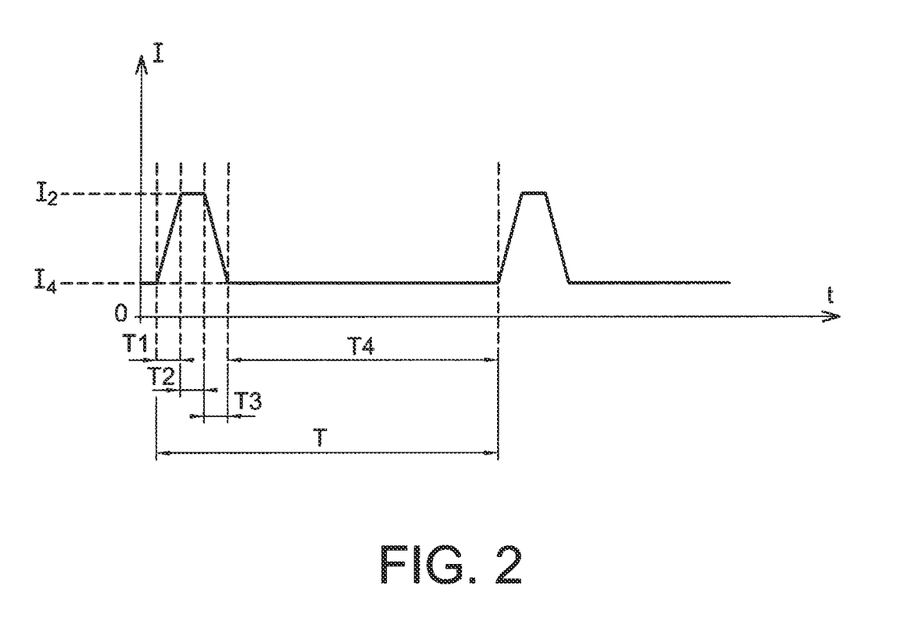
FIG. 2 represents a neutron emission spectrum in accordance with the invention.

The neutron generators G1 and G2 emit neutrons some of which are directed towards the object to be studied. The neutron generators G1 and G2 operate simultaneously (FIG. 2 represents the change over time of the emission intensity of the neutrons emitted simultaneously by the neutron generators G1 and G2). A gamma radiation γ1 results from the interaction of the neutrons emitted by generator G1 with the object to be studied and a gamma radiation γ2 results from the interaction of the neutrons emitted by generator G2 with the object to be studied. Each of the gamma radiations γ1 or γ2 may be a capture gamma radiation or an inelastic gamma radiation.

Each of the detectors D1 or D2 is able to detect a capture and/or inelastic radiation. However, detector D1 is preferentially adapted for the detection of inelastic gamma radiation by the associated particle method (detector D1 is thus chosen for its high detection efficiency and its satisfactory time resolution) and detector D2 is preferentially adapted for the detection of capture gamma radiation by the pulsed neutron interrogation method (detector D2 is thus chosen for its satisfactory energy resolution). Detector D1 is, for example, a high-efficiency scintillation crystal, and detector D2 is, for example, a high-resolution energy semiconductor crystal.

FIG. 1 represents the case in which a nucleus of the chemical compound X1 is subjected to an interaction with a neutron from the generator G1, causing the emission of a radiation γ1 which is detected by the detector D1, and in which a nucleus of the second chemical compound X2 is subjected to an interaction with a neutron from the generator G2, causing the emission of a γ2 radiation which is detected by detector D2. A neutron originating from generator G1 causes the emission of a radiation γ1 in object O, here of the inelastic type, this radiation γ1 being detected in the detector D1, and a neutron emitted by generator G2 is slowed as a consequence of multiple collisions in object O, and then causes the emission of a capture gamma radiation γ2, this radiation γ2 being detected in detector D2. However, the invention concerns all other possible cases of detection such as, for example, cases in which the nuclei of a given chemical element are detected using two gamma radiations γ1 and γ2, or only by one of the two radiations γ1 or γ2.

In a known manner, the associated particle neutron generator G1 emits neutrons by the action of a continuous beam F1 of deuterium on a tritium target T1. The emission of neutrons occurs by a reaction in which an α particle is produced at the same time as a neutron. The α particle is detected by a position-sensitive detector L which belongs to the generator G1. The position-sensitive detector L consists, for example, of a set of N elementary detectors $d_k$ (k=1, 2, ..., N) assembled in the form of the matrix. The knowledge of the elementary detector $d_k$ which, among the N detectors, detects the particle α, enables the direction in which the α particle has been emitted to be located accurately. In another embodiment of the invention the position-sensitive detector L does not consist of a set of elementary detectors, but of a single sensor unit on which several sensors are positioned, and the α particle is then positioned by a barycentric calculation. Since the α particle and the neutron are emitted in roughly opposing directions, knowledge of the direction in which the α particle is emitted enables the direction in which the neutron is emitted to be known. As soon as an α particle is detected by the detector L, a signal S1 revealing the detection of the α particle is transmitted to the electronics circuit E. Signal S1 is a synchronisation signal which authorises the electronic circuit E to respond to a pulse delivered by the detector D1. Signal S1 also includes a data item which identifies the direction in which the neutron has been emitted (the elementary detector $d_k$ which detected the α particle in the case of a matrix detector, or the position of the detection in the case of a sensor unit). According to the embodiment described above, synchronisation signal S1 is delivered by detector L. In another embodiment of the invention, synchronisation signal S1 is delivered by the detector D1, if the latter has received a gamma radiation pulse.

The pulsed neutron generator G2 emits neutrons in the form of intense neutron pulses by the action of a pulsed beam F2 of deuterium on a tritium target T2. The pulsed neutron generator G2 also delivers an electric pulse signal S2 which reproduces the temporal shape of the neutron pulses. Signal S2 is transmitted to the electronic processing circuit E. Signal S2 controls the electronic processing circuit E in order to respond to and identify the pulses delivered by the detector D2, firstly, during each intense neutron pulse and, secondly, between two successive intense neutron pulses. Signal S2 also controls the electronic processing circuit E in order to respond to the pulses delivered by the detector D1 only between the successive intense neutron pulses. Indeed, signal acquisition by the associated particle technique must not occur during the emission of the intense neutron pulses, since this would result in a great degradation of the signal-to-noise ratio.

Database $B_0$ stores the inelastic events EV0 detected by the detector D2, during the intense neutron pulses, in the form of a list of the energies E0 deposited in the detector D2, these energies being proportional to the amplitude of the electrical pulses generated by the detector D2 under the action of the gamma radiation. In the remainder of the description these energies will be named "energies of the detected pulses" for the purposes of simplification.

Database $B_1$ stores the inelastic and capture events EV1 detected by the detector D2, between the intense neutron pulses, in the form of a list of the energies E1 of the pulses which are generated by the detector D2 under the action of the gamma radiation.

Database $B_2$ stores the residual inelastic and capture events EV2 which are detected, using the associated particle technique, by the detector D1, between the intense neutron pulses. As will be stipulated in due course, each event EV2 contains a set of data, namely: a gamma energy, a period of coincidence between detection of the α particle and that of the associated γ radiation, and a data item giving the position of detection of the α particle.

The computer C calculates the alert signal S(alerte) on the basis of the data stored in the databases $B_0$, $B_1$, $B_2$ and of reference data stored in the databases $B_{RC}$ and $B_S$, as will be described in due course, with reference to FIG. 3.

FIG. 2 represents the intensity I of the neutrons which are emitted simultaneously by the neutron generators G1 and G2. Neutrons are continuously emitted by the tube G1 with an intensity $I_4$ and intense neutron pulses are emitted with a period T by the neutron generator G2. During an intense neutron pulse, the overall intensity of the neutrons emitted by the tubes G1 and G2 changes from $I_4$ to $I_2$ over a duration T1 (for example equal to 1 µs), roughly keeps value $I_2$ during a period T2 (for example a few tens of microseconds) and falls from $I_2$ to $I_4$ during a duration T3 which is roughly equal to T1. After this, a T4 duration separates the end of an intense neutron pulse from the start of the following intense neutron pulse. Due to the simultaneous character of the emission of neutrons by the G1 and G2 tubes, it must be emphasised that, unlike the prior art known in the field of pulsed neutron interrogation, the number of neutrons emitted does not stand at zero between the intense neutron pulses, but keeps a non-zero value.

During the emission duration T2 of an intense neutron pulse, and during the duration T4 separating two intense neutron pulses, the synchronisation signal S2 puts the electronic circuit E into a state of waiting for reception of gamma radiation originating from detector D2. If a gamma radiation is detected during the phase of duration T2 of intense neutron emission, it is due, most probably, to the reactions of the fast neutrons which cause an inelastic gamma radiation and, with a low probability, to the thermal neutrons. If such radiation is detected, it is measured and then converted, preferentially, in the form of a digital data item, by the electronic circuit E. The digital data representing the energies measured in this manner constitutes the EV0 events (i.e. the energies E0 of the pulses) which are stored in database $B_0$. If a gamma radiation is detected during the duration T4 separating two intense neutron pulses, it may originate from a capture reaction or from an inelastic reaction. The energy of such a radiation is measured and then converted, preferentially, in the form of a digital data item, by the electronic circuit E. The digital data representing the energies detected in this manner constitutes the EV1 events (i.e. the energies E1 of the pulses) which are stored in database $B_1$.

In addition, if an α particle is detected during duration T4, the signal S1 puts the electronic circuit E into a state of waiting for a gamma radiation detected by detector D1. If a gamma radiation is detected coinciding with the α particle, the energy of the gamma radiation is measured and then converted, preferentially, in the form of a digital data item, by the electronic circuit E. The electronic circuit E also calculates the duration $T_{\alpha\gamma}$ separating the detection of the α particle from the detection of the gamma radiation. Database $B_2$ stores the EV2 events which are detected by detector D1 in the form of digital data. An EV2 event gathers the energy E2 of the detected gamma radiation, the duration $T_{\alpha\gamma}$ and a data item $i_k$ which identifies the position at which the α particle has been detected in the position-sensitive detector L. A proportion of these events is due to gamma capture radiation. This proportion of events is preferentially eliminated from the gamma spectrum for the observed object, as will be described in due course with reference to FIG. 3.

All the measurements made over a period T (T=T1+T2+T3+T4) constitute a measurement cycle. After Nm measurement cycles, for example 600000 measurement cycles corresponding to a total measuring duration of approximately ten minutes, a processing cycle is undertaken.

Figure 3:
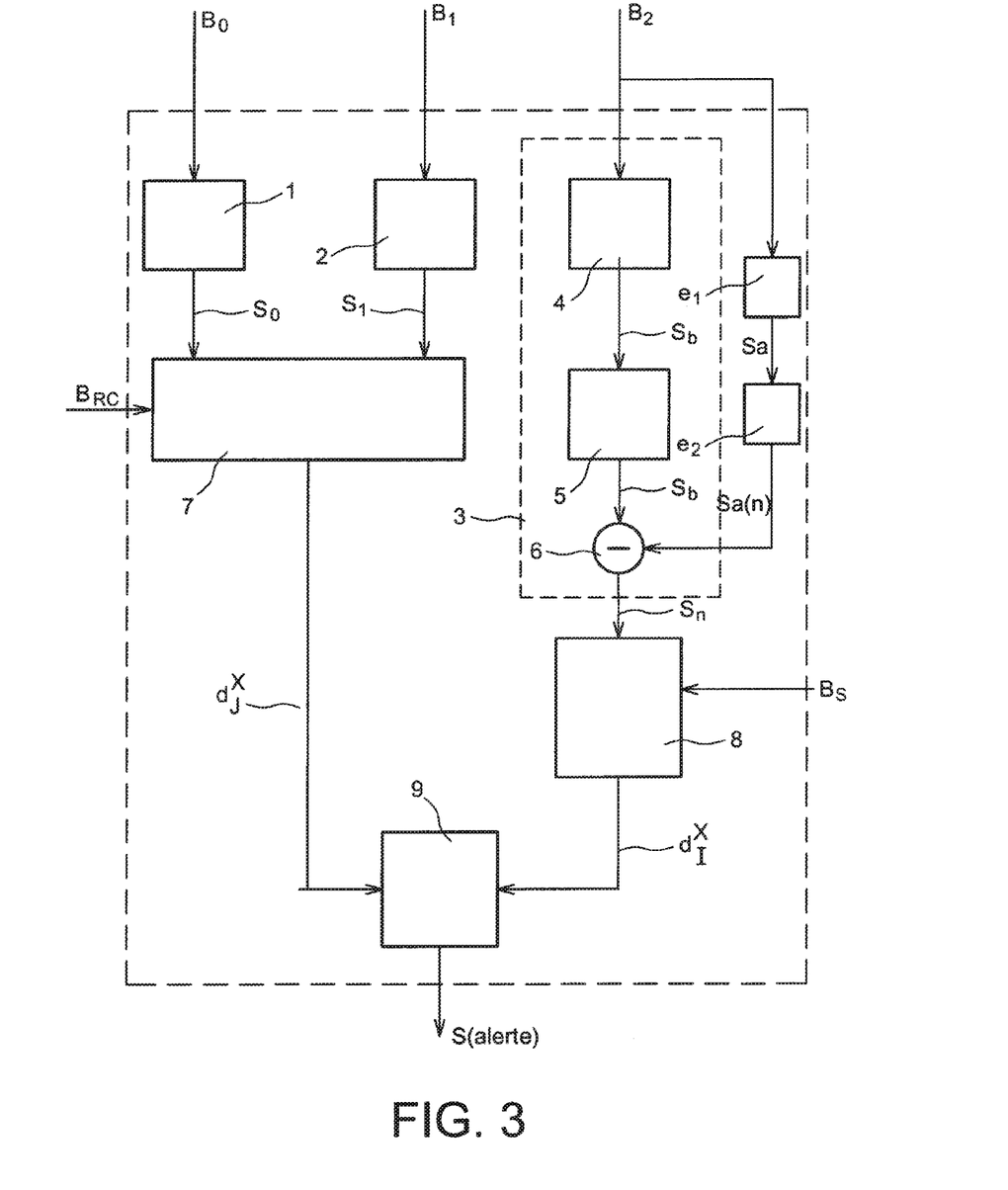
FIG. 3 represents the steps of a processing cycle of the non-intrusive detection method of the invention.

FIG. 3 represents the different steps implemented in a processing cycle of the invention. A processing cycle is implemented by the computer C.

A processing cycle firstly includes a set of steps of construction of spectra, namely:
 a step 1 of construction of a gamma spectrum $S_0$ from data stored in database $B_0$,
 a step 2 of construction of a gamma spectrum $S_1$ from data stored in database $B_1$, and
 a step 3 of construction of a gamma spectrum Sn without random noise from data stored in database $B_2$, where step 3 itself consists of a step 4 of selection of the events stored in database $B_2$ to determine, from among these events, those which correspond to the studied object, a step 5 of construction of a raw gamma spectrum Sb of the studied object from the events selected on conclusion of step 4, of a succession of steps e1, e2 to form a standardised random noise spectrum Sa(n) from the events stored in database $B_2$ and a step 6 of subtraction of the raw gamma spectrum Sb and of the standardised random noise spectrum Sa(n) to form the spectrum Sn without random noise, which then includes only the inelastic events caused by the fast neutrons in the studied object.

Steps 1, 2 and 3 of construction of spectra are followed by spectra processing steps, namely:
 a step 7 of a search for a chemical element (or chemical elements) on the basis of spectra $S_0$ and $S_1$, and
 a step 8 of a search for a chemical element (or chemical elements) on the basis of spectrum Sn.

Steps 7 and 8 of spectra processing are, for their parts, followed by a decision-making step 9.

A step of construction of a spectrum from stored data is understood to mean a step, known in the art, of construction of histograms of energies of the events associated with this data.

Step 3 of construction of the spectrum Sn without random noise on the basis of data stored in database $B_2$ will now be described.

The inelastic and capture events EV2 which are stored in database $B_2$ consist only of events which occur between the neutron pulses. Electronic circuit E includes, to this end, means which select, on the basis of the signal S2 originating from the pulse generator G2, the events detected by the detector D1 in the desired time spans.

As was mentioned above, step 3 includes a step 4 of selection of the events stored in database $B_2$. Step 4 of selection of the events stored in database $B_2$ relies on the known associated particle technique. This step is a step known in the art which enables, from among all the events in database $B_2$, those concerning the studied object to be determined.

On the basis of the events selected in this manner in step 4, the raw gamma spectrum of the object studied Sb in step 5 is constructed. Step 5 is a step known per se, like the previously mentioned steps 1 and 2. Step 5 is followed by a step 6 which subtracts from spectrum Sb the standardised random noise spectrum Sa(n). The standardised random noise spectrum Sa(n) is constructed by the successive steps e1 and e2, using spectral data stored in database B2. A random noise spectrum Sa is firstly formed from the spectral data stored in database $B_2$ (step e1) and the standardised random noise spectrum Sa(n) is then formed from the random noise spectrum Sa (step e2). Formation of the standardised random noise spectrum Sa(n) is stipulated below with reference to FIG. 4.

Figure 4:
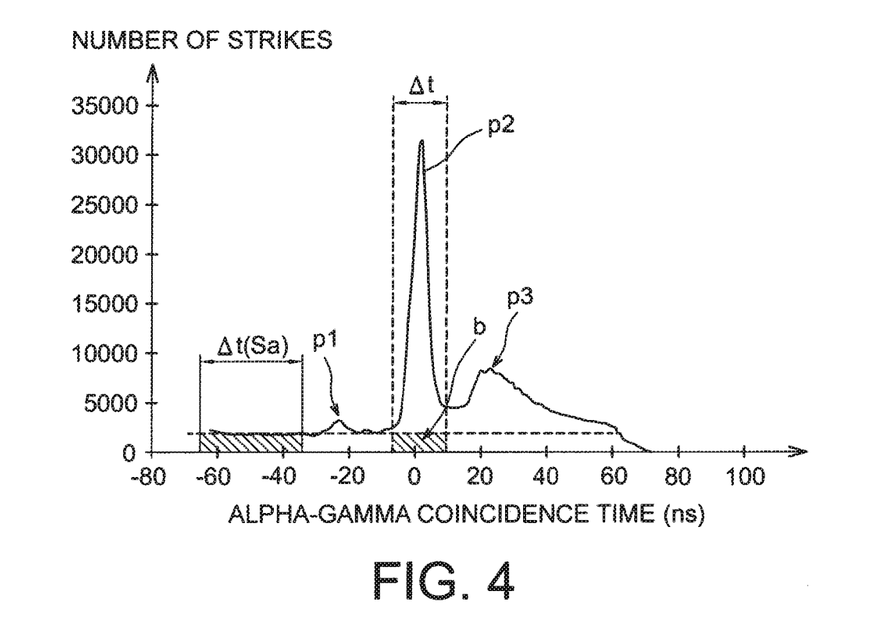
FIG. 4 represents an example of a time spectrum for the associated particle technique.

FIG. 4 represents an example of a time spectrum obtained using the associated particle technique. This spectrum represents the periods separating the detection of the alpha particle and of the gamma radiation, from which periods it is possible to deduce the neutron flight times. The spectrum of FIG. 4 includes, as an example, a noise level b representing the level of fortuitous coincidences, a level above which a peak p1 of very low amplitude is illustrated, corresponding to the photons induced in the generator G1, a peak p2 of high amplitude representing the true coincidences of the studied object and a peak p3 of medium amplitude representing the events which are not due to the studied object. The temporal width Δt of peak p2 is the time span relative to the studied object. Step e1 consists, for example, in selecting the events of the time spectrum in a time span Δt(Sa) which is negative relative to the time span relative to the studied object, and separate from the time span relative to the studied object, and in then constructing the random background noise spectrum Sa due to the fortuitous coincidences from the events selected in this manner. The duration Δt(Sa) is preferentially higher than or equal to the time span Δt of the studied object in order to obtain an improved statistical accuracy. Step e2 then consists in standardising the spectrum Sa at width Δt of the time span of the studied object. The standardisation factor is equal to Δt/Δt(Sa).

The standardised spectrum Sa(n) delivered on conclusion of step e2 is then deducted from the unprocessed spectrum Sb in step 6. This gives the gamma spectrum without the random noise Sn of the studied object. The presence of a chemical element (or chemical elements) is then sought, from spectrum Sn, using a processing algorithm which is implemented, in a known manner, by step 8 (cf. FIG. 3). The search for a chemical element (or chemical elements) is made using reference data archived in a preestablished list contained in a database Bs. Database Bs contains full spectrum data for each of the chemical elements which may be detected. The energy resolution of detector D1 does not allow processing by line, unlike detector D2. Step 8 therefore implements a deconvolution of the whole of spectrum Sn in order to extract the relative contribution of each element present. The deconvolution is undertaken by an adjustment algorithm using the data contained in database Bs. The proportion of events in Sn associated with an element X is then standardised using the total number of strikes in Sn. The percentage $F_X$ of the element X in the complete spectrum is then calculated with the variance σ(Fx) associated with it. An element X is considered to be detected if, for example, the following inequality is confirmed:

$$\sigma(F_X)/F_X < 50\%$$

Step 7 (cf. FIG. 3) of the search for a chemical element (or chemical elements) using the spectra $S_0$ and $S_1$ is undertaken using a processing algorithm A1.

Figure 5:
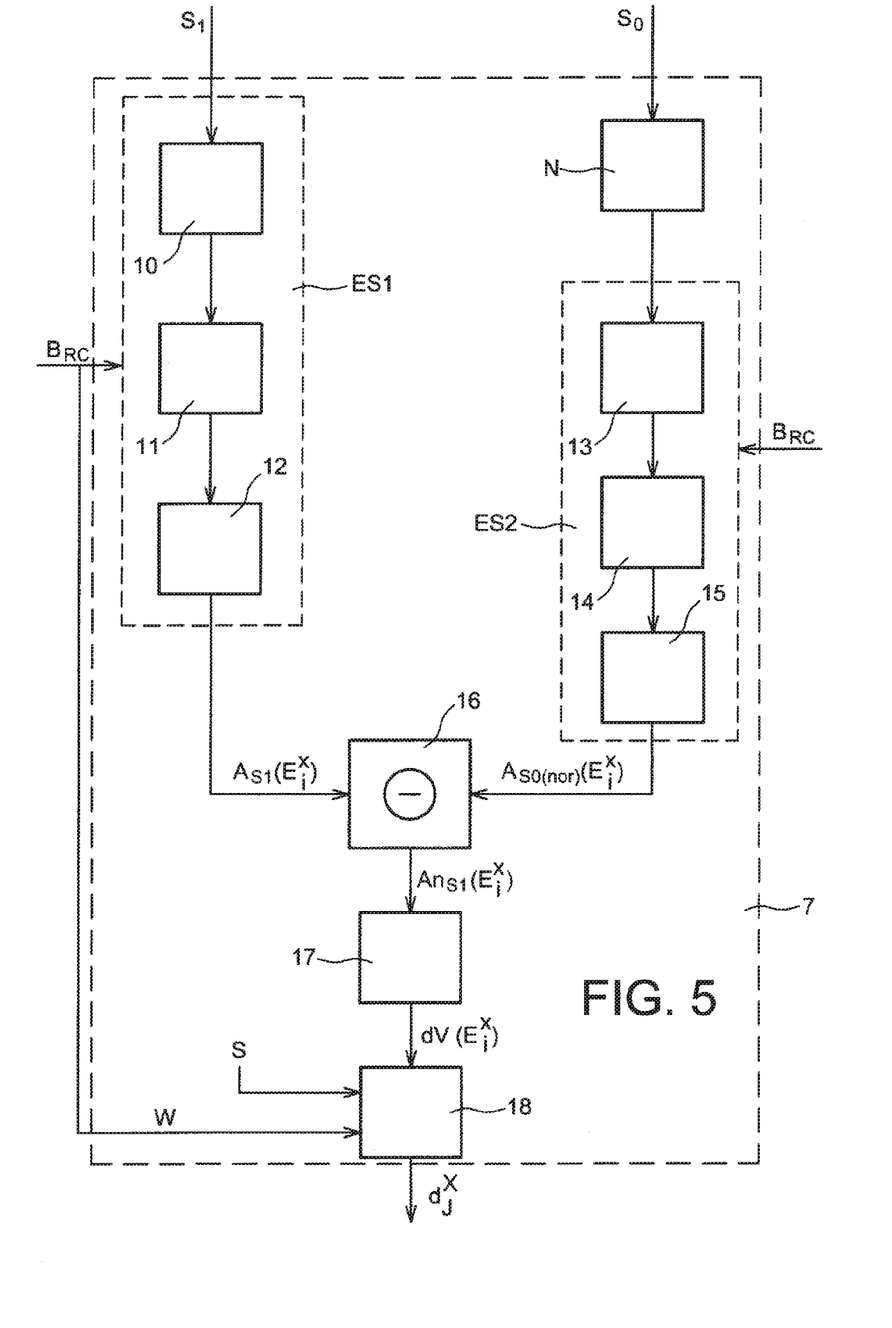
FIG. 5 represents elementary steps of a particle step of the processing cycle represented in FIG. 3.

FIG. 5 illustrates the elementary steps implemented by algorithm A1. Algorithm A1 determines the presence of chemical elements corresponding to gamma lines archived in the reference database $B_{RC}$. Algorithm A1 includes the search for possible interferences of inelastic radiation using the analysis of spectrum $S_0$.

In a manner known per se, every element X sought is characterised by a set of n energy capture gamma lines $E1^X$, $E2^X$, ..., $En^X$ characteristic of the natural isotopes of element X. In the context of the invention, there is a risk of interference of the capture lines corresponding to sought elements with capture lines of elements other than the sought elements, or with inelastic lines due to the residual emission of generator G1 between the intense pulses delivered by generator G2. The purpose of algorithm A1 is to select, from a list of lines associated with each element X of interest, those of sufficient intensity and of a low risk of interference.

Algorithm A1 includes a step ES1 of processing of the spectrum $S_1$, a step N of standardising the spectrum $S_0$, a step ES2 of processing of the standardised spectrum, a step of subtraction 16 which subtracts the result of the processing step ES2 from the result of the processing step ES1, a step 17 of line validation and a step 18 of determination of the presence of an element.

Figure 6:
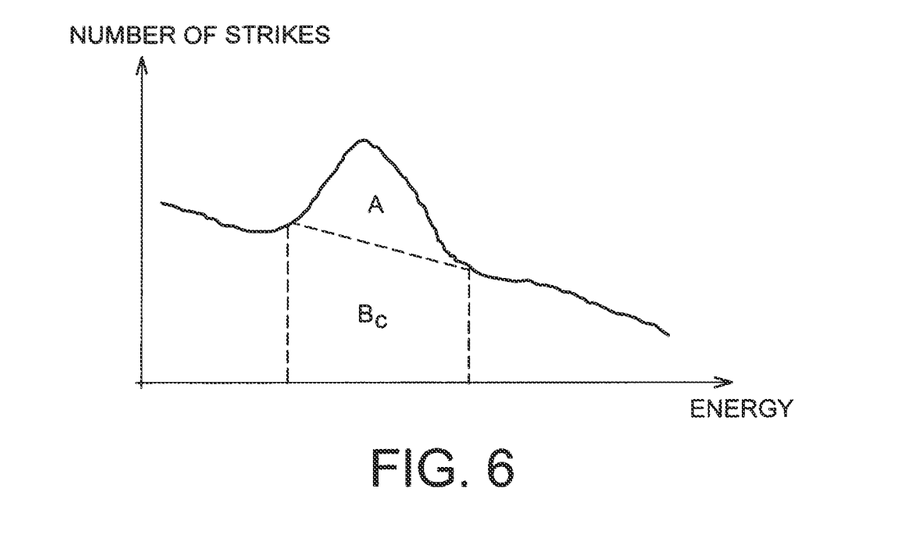
FIG. 6 represents a peak of detection of a gamma line in a gamma spectrum.

Processing step ES1 includes, in succession, a step 10 of search for peaks, a step 11 of extraction of net areas, and a step 12 of validation of line detection. Each of these steps is a step known in the art. Step 10 of searching for peaks is followed, for each detected peak, by a step 11 of extraction of the net area A of the peak. FIG. 6 represents a gamma spectrum peak. The net area A of the peak represented in FIG. 6 is the area of the peak exceeding the Compton background noise level Bc. A line $E^X_i$ of an element X is considered to have been detected in the spectrum if the net area $A_{S1}(E^X_i)$ of the line $E^X_i$ satisfies, for example the following equation:

$$\sigma[A_{S1}(E^X_i)]/A_{S1}(E^X_i) < 50\%,$$

where $\sigma[A_{S1}(E^X_i)] = [A_{S1}(E^X_i) + 2Bc_{S1}(E^X_i)]^{1/2}$, and where $Bc_{S1}(E^X_i)$ is the Compton background noise associated with line $E^X_i$.

This criterion corresponds approximately to a 95% confidence level, and can be adjusted according to the desired false alarm rate.

The purpose of the standardisation step N is to eliminate the undesirable components contained in spectrum $S_0$. These undesirable components are peaks corresponding to inelastic radiation due to the residual emission of generator G2 between the intense pulses, which peaks are located at a proximity from one of the capture lines $E1^X$, $E2^X$, ..., $En^X$ of a sought elements such that the energy separation power of detector D2 does not enable the inelastic line to be distinguished from the capture line. Standardisation step N includes the calculation of a standardisation factor F. Standardisation factor F is roughly proportional to the number of neutrons of intensity $I_4$ emitted during the duration T4 separating two pulses, and roughly inversely proportional to the number of neutrons emitted during the duration T2 of a neutron pulse of intensity $I_2$.

Factor F can thus be, for example, given by the following equation:

$$F = (I_4 \times T_4)/(I_2 \times T2) \times [(1-TM(T_4))/(1-TM(T_2))],$$

where TM(T4) and TM(T2) are, respectively, an idle time of the electronic processing unit E which process the electrical signals resulting from the detection of the gamma radiation detected during the T4 durations, and an idle time of the electronic processing unit E which process the electrical signals resulting from the detection of the gamma radiation detected during the T2 durations.

Factor F can also be obtained empirically by measuring, in a calibration phase undertaken under conditions similar to those of an inspection measurement, during the T2 and T4 durations, the intensities of inelastic gamma lines. The gamma lines used for calculating factor F are then chosen precisely for their intensity, for their energy, and because they have no known interference with capture radiation. The standardised gamma spectrum $S_0(n)$ is then formed by multiplying the number of strikes present in each energy channel of the gamma spectrum $S_0$ by factor F.

The processing step ES2 follows standardisation step N. Processing step ES2 includes, in a manner known in the art, a search for the peaks present in the standardised spectrum $S_0(n)$ (step 13), an extraction of the net areas $A_{S0(nor)}(E^X_i)$ of the peaks of the standardised spectrum (step 14) and a step of line detection validation (step 15). From each net capture area $A_{S1}(E^X_i)$ of line $E^X_i$ delivered after step 12, in step 16 the standardised net area $A_{S0(nor)}(E^X_i)$ delivered after step 15 is subtracted. If there is no peak detected in step 13 (which is the most frequent case), the standardised net area $A_{S0(nor)}(E^X_i)$ relative to energy $E^X_i$ is defined as being equal to zero. On conclusion of step 16 a net area $An_{S1}(E^X_i)$ without inelastic contributions is then obtained, namely:

$$An_{S1}(E^X_i) = A_{S1}(E^X_i) - A_{S0(nor)}(E^X_i).$$

The capture line of an element X is confirmed in step 17, if the following relationship is, for example, confirmed:

$$\sigma[An_{S1}(E^X_i)]/An_{s1}(E^X_i) < 50\%, \text{ where:}$$

$$\sigma[An_{S1}(E^X_i)]^2 + \sigma[A_{S1}(E^X_i)]^2 + \sigma[A_{S0(nor)}(E^X_i)]^2 = [A_{S1}(E^X_i) + 2Bc_{S1}(E^X_i)] + F^2[A_{S0}(E^X_i) + 2Bc_{S0}(E^X_i)]$$

Database $B_{RC}$ includes weight data W relative to each line which may be detected. The weight data W of a line of an element X is a function of the probability which the line has of being detected, of the risk of interference of the line with identical lines originating from elements other than element X, and of the total number of lines corresponding to element X. The sum of the weights of all the lines of a given element is equal to 1. Using the weight data W stored in the database $B_{RC}$ and the validation information $dV(E^X_i)$ delivered, on conclusion of step 17, for each energy capture line $E^X_i$, step 18 calculates the sum weighted with the weights of the lines detected for element X. The fact of using several lines, and of not therefore being limited to the most intense line, enables the risk that the most intense line will in fact originate from an unsought element, the possible interference of which with this line has not been allowed for, to be limited. The other lines expected for element X, although potentially less intense, therefore enable the presence of the element to be confirmed. The most intense line has, in principle, the highest weight W, unless it is subject to a possible known interference with an unsought element, which is often present in interrogated objects or their environment. The definition of the weight of each line $E1^X, E2^X, \ldots, En^X$ of a sought element therefore results from a compromise between detection sensitivity and risk of interference. An element X is considered as detected if the sum of the weights of the detected lines calculated is greater than an adjustable threshold S, equal for example to 0.5. A binary data item $d_j^X$ is delivered on conclusion of step 18 to reveal whether or not element X has been detected.

Step 9 (cf. FIG. 3) is a decision-making step which is implemented, using algorithm A4, on the basis of the data $d_j^X$ and $d_j^X$ delivered on conclusion of the respective steps 8 and 7. An alert signal S(alerte) is delivered on conclusion of the decision-making step if one or other of the data items $d_j^X$ and $d_j^X$ confirms the presence of chemical element X. The decision-making step delivers a signal signifying that the chemical element is absent if none of the data elements capable of confirming or refuting the presence of the chemical element confirms its presence. In the case of certain illegal substances it is the proportion of certain chemical elements which enables the presence of these substances to be ruled out. To this end, according to an improvement of the method of the invention, a calculation of the relative proportions of certain detected chemical elements, for example the relative proportions of Carbon (C), Nitrogen (N) and Oxygen (O) is made, to differentiate drugs and explosives from inoffensive substances which also contain these chemical elements.

The invention claimed is:

1. A method for detecting the presence of a chemical element (X) in an object by emission of neutrons onto the object, characterized in that the emission of neutrons onto the object is constituted, firstly, by a continuous emission of neutrons originating from an associated particle neutron generator (G1) able to implement a radiation detection by means of an associated particle technique and, secondly, by an emission of neutron pulses which are superimposed on the continuous emission of neutrons, where the neutron pulses originate from a pulsed neutron generator (G2) able to implement a radiation detection by means of a pulse neutron interrogation technique, said pulsed neutron generator generating neutron pulses of pulse duration T2, where two successive neutron pulses are separated by a duration T4, and where the continuous and pulsed emissions of neutrons onto the object produce a gamma capture radiation and an inelastic gamma radiation.

2. The method according to claim 1, characterized in that it includes:

detection, using the associated particle technique, during the T4 durations separating the pulses of duration T2, of the inelastic gamma radiation and of the capture gamma radiation, formation, in a neutron flight time span relative to the object, of a first gamma spectrum ($S_b$) on the basis of the inelastic gamma radiation and of the capture gamma radiation detected in the detection step using the associated particle technique, formation ($e_1$), in a time span separated from the neutron flight time span relative to the object or any other neutron flight time span relative to any other object likely to be in the vicinity of the object, of a random background noise spectrum (Sa) relative to the fortuitous coincidences, on the basis of the inelastic gamma radiation and of the capture gamma radiation detected in the detection step using the associated particle technique, formation (e2), on the basis of the random background noise spectrum relative to the fortuitous coincidences (Sa), of a standardized random background noise spectrum (Sa(n)) over the time span relative to the object, subtraction of the standardized random background noise spectrum (Sa(n)) from the first gamma spectrum ($S_b$) to form a second gamma spectrum ($S_n$), and a step of searching for the presence of a chemical element in the object on the basis of the second gamma spectrum ($S_n$) and of spectra of chemical elements of reference which may be detected ($B_s$) in order to deliver a first data item ($d_i^X$) able to reveal the presence or absence of the chemical element (X) in the object.

3. The method according to claim 2, characterized in that it includes, in addition:

detection, using the pulsed neutron interrogation technique, of the capture gamma radiation and of the inelastic gamma radiation, firstly during the T2 pulse durations, and secondly during the T4 durations separating the pulses of duration T2, formation of a third gamma spectrum ($S_1$), on the basis of the detected gamma capture radiation and inelastic gamma radiation, during the T4 durations, using the pulsed neutron interrogation technique, formation (ES1), on the basis of the third gamma spectrum ($S_1$), of a net capture area ($A_{S_1}(E_i^X)$) representative of at least one capture line ($E_1^X, E_2^X, \ldots, E_n^X$) of the chemical element (X), formation of a fourth gamma spectrum ($S_0$) consisting of multiple energy channels, on the basis of the inelastic radiation detected during the T2 pulse durations, using the pulsed neutron interrogation technique, formation (N) of a standardized gamma spectrum ($S_{(nor)}$) on the basis of the fourth gamma spectrum ($S_0$), where the standardized gamma spectrum ($S_{0(nor)}$) is formed by multiplying the content of each energy channel of the fourth gamma spectrum by a standardization factor (F) roughly proportional to the number of neutrons emitted during a T4 duration, and roughly inversely proportional to the number of neutrons emitted during a T2 duration, formation (ES2), on the basis of the standardized gamma spectrum ($S_{0(nor)}$), of a standardized net area ($A_{S0(nor)}(E_i^X)$) representing an inelastic gamma radiation background noise.

a step of subtraction of the standardized net area ($A_{S0(nor)}(E_j^X)$) representing an inelastic gamma radiation background noise from the net capture area ($A_{S1}(E_i^X)$) representative of at least one capture line of chemical element.

a step of validation of the presence or absence of the chemical element (X) in the object according to the results of the subtraction step, and if the presence of the chemical element (X) is validated in the object, an additional step which delivers a second data item ($d_j^X$) able to confirm or refute the validation of the presence of the chemical element (X) on the basis of the result of the validation step and of weight data ($W(E1^X) W(E2^X) \ldots, W(En^X)$) relative to the various capture radiation gamma lines of the chemical element (X), where these weights are attributed according to a probability of detection and a risk of interference associated with each line.

4. The method according to claim 3, in which the standardization factor (F) is given by the following equation:

$$F=(I_4 \times T4)/(I_2 \times T2) \times [(1-TM(T4))/(1-TM(T2))],$$

where TM(T4) and TM(T2) are, respectively, an idle time of an electronic processing unit (E) which process the electrical signals resulting from the detection of the gamma radiation during the T4 durations, and an idle time of an electronic processing unit (E) which process the electrical signals resulting from the detection of the gamma radiation detected during the T2 durations.

5. The method according to claim 3, in which a decision-making step delivers an alert signal (S(alerte)) if the first data item ($d_1^X$) or the second data item ($d_j^X$) confirms the presence of the chemical element.

6. The method according to claim 5, in which, if the presence of several chemical elements is confirmed it includes an additional step of calculation of relative proportions of all or part of the chemical elements the presence of which is confirmed.

7. The method according to claim 2, in which the detection, using the associated particle technique, of the capture gamma radiation and of the inelastic gamma radiation during the T4 durations separating the pulses of duration T2 is undertaken by a detector (D1) which is preferentially adapted for the detection of inelastic gamma radiation.

8. The method according to claim 3, in which the detection, using the pulsed neutron interrogation technique, of the capture gamma radiation and of the inelastic gamma radiation, firstly, during the pulses of duration T2 and, secondly, during the T4 durations separating the pulses of duration T2, is undertaken by a detector (D2) which is preferentially adapted for the detection of capture gamma radiation.

* * * * *